United States Patent
Ilkov

(10) Patent No.: US 8,605,283 B2
(45) Date of Patent: Dec. 10, 2013

(54) APPARATUS AND METHOD FOR INCREASING COLLECTION EFFICIENCY IN CAPILLARY BASED FLOWCYTOMETRY

(75) Inventor: Fedor Ilkov, San Jose, CA (US)

(73) Assignee: EMD Millipore Corporation, Billerica, MA (US)

( * ) Notice: Subject to any disclaimer, the term of this patent is extended or adjusted under 35 U.S.C. 154(b) by 0 days.

(21) Appl. No.: 13/457,356

(22) Filed: Apr. 26, 2012

(65) Prior Publication Data

US 2012/0281216 A1    Nov. 8, 2012

Related U.S. Application Data

(60) Provisional application No. 61/482,946, filed on May 5, 2011.

(51) Int. Cl.
    *G01N 21/00*    (2006.01)
(52) U.S. Cl.
    USPC .......................................... 356/440; 356/441
(58) Field of Classification Search
    USPC ......... 356/432–442, 244, 246, 427, 335–343, 356/311, 317, 318, 417; 382/128, 133, 134; 422/73, 68.1, 63, 50; 250/432 R, 458.1, 250/461.2, 222.2, 222.1, 373
    See application file for complete search history.

(56) References Cited

U.S. PATENT DOCUMENTS

| | | | |
|---|---|---|---|
| 4,904,085 A | 2/1990 | Spillman et al. | |
| 4,986,657 A | 1/1991 | Ohe | |
| 5,434,664 A | 7/1995 | Sapp | |
| 5,547,849 A | 8/1996 | Baer et al. | |
| 5,895,920 A | 4/1999 | Carlsson | |
| 6,184,990 B1 | 2/2001 | Amirkhanian et al. | |
| 7,391,512 B2 | 6/2008 | Fouquet et al. | |
| 7,768,634 B2 | 8/2010 | Uto et al. | |
| 2005/0104008 A1* | 5/2005 | Oostman et al. | 250/458.1 |
| 2008/0283773 A1 | 11/2008 | Goix et al. | |

OTHER PUBLICATIONS

PCT, International Search Report and Written Opinion in PCT/US2012/035295, Sep. 24, 2012, 11 pages.

* cited by examiner

*Primary Examiner* — Tri T Ton
(74) *Attorney, Agent, or Firm* — Houst Consulting

(57) ABSTRACT

In a particle analyzing apparatus including a capillary for passing through a fluid containing particles to be analyzed, an optical system is employed to collect fluorescent light emitted from particles or substances labeled to the particles with improved collection efficiency preserving resolution of the instrument. The optical system may include a first collection lens attached to the capillary and a first reflection element arranged adjacent to the first collection lens configured to reflect fluorescent light of one or more wavelengths. The optical system may include a second collection lens attached to the capillary and a second reflection element arranged adjacent to the second collection lens configured to reflect fluorescent light of one or more wavelengths.

10 Claims, 7 Drawing Sheets

APPARATUS AND METHOD FOR INCREASING COLLECTION EFFICIENCY IN CAPILLARY BASED FLOWCYTOMETRY

CROSS-REFERENCE TO RELATED APPLICATIONS

This application claims priority under 35 USC §119(e) to U.S. Provisional Patent Application Ser. No. 61/482,946 filed May 5, 2011, the disclosures of which are incorporated herein by reference.

BACKGROUND

This invention relates generally to detection and analysis of particles in fluid samples and in particular to apparatuses and methods for increasing light collection efficiency in capillary based flow cytometry.

Flow cytometry finds a variety of applications throughout the life sciences including clinical diagnostics and immunology, protein and nucleic acid detection, hematology, and oncology. For example, flow cytometry can be used to identify and count particles, cells or microorganisms with specific characteristics in a fluid sample. In a typical flow cytometer, particles to be analyzed are transported in a flowing fluid to an analyzing region where they are illuminated with a focused output beam of a light source. Scatter light and/or fluorescence emitted by the illuminated sample particles are collected and separated according to emission angle and wavelength using optical systems, and detected by photo detectors. The detected scatter light and/or fluorescence in the form of pulses with amplitudes and temporal profiles may be characteristic of the particles' sizes, shapes, and structures etc. A computer system is commonly used to convert analog light signals into digital data streams for subsequent processing and analysis.

The light collection efficiency (CE) of an optical system in a flow cytometer determines the sensitivity and throughput of the instrument. Numerical aperture is a measure of the collection power of an optical system. The collection efficiency increases with the numerical aperture (NA) of the collecting optics as $CE \sim NA^2$. Using more powerful, i.e., high NA optics, may provide a straight-forward increase in collection efficiency. However, there is a significant drawback of using high NA optics in capillary based flow cytometry because the sensitivity to a particle position within an analyzing region inside a capillary also increases with the same quadratic dependence on the numerical aperture of the collecting optics (depth-of-field $\sim 1/NA^2$), resulting in high coefficient of variation (CV) values or decreased resolution of the instrument. Therefore, in current capillary based flow cytometry in which a capillary bore size defines the area of sample localization for interrogation process, compromises are often empirically found in the configurations of the capillary and light collection optics considering factors such as the usability and availability of the capillary and the desired resolution, sensitivity and manufacturability of the instrument. For instance, in a conventional capillary based cytometer, collecting optics with a numerical aperture of about 0.4-0.5 is used, which provides a collection efficiency of fluorescence about only 3 percent. The low collection efficiency substantially restricts achievable sensitivity and/or throughput of the instrument. With improved air-spaced optics, collection efficiency may increase but is limited by physics to NA=0.69 and collection efficiency to about 10 percent.

Accordingly, there is a need for improved collection efficiency in flow cytometry without significantly compromising the resolution of the instrument. There is a need for increased sensitivity and/or throughput of flow cytometry without significantly compromising the manufacturability or construction cost of the instrument.

SUMMARY

Optical systems configured to improve light collection efficiency of particle analyzing apparatuses are provided. Also provided are flow cells including a microcapillary integrated with one or more micro lenses. Particle analyzing apparatuses including the provided optical systems and/or flow cells are also provided. Other embodiments are described further herein.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of optical systems, flow cells, and particle analyzing apparatuses including the optical systems and/or flow cells are described. It is to be understood that the invention is not limited to the particular embodiments described as such which may, of course, vary. While various embodiments are described in connection with capillary based flow cytometry, it will be appreciated that they can also be practiced in other particle analyzing devices such as sheath flow cytometry. It is also to be understood that the terminology used herein is for the purpose of describing particular embodiments only, and is not intended to be limiting since the scope of the invention will be defined by the appended claims, along with the full scope of equivalents to which such claims are entitled. In addition, various embodiments are described with reference to figures. It should be noted that the figures are intended to facilitate the description of specific embodiments and they are not intended as an exhaustive description or as a limitation on the scope of the invention.

As used herein, the term "particles" refers to any particles that can be detected and analyzed by the particle analyzing apparatuses described herein, including synthetic particles, beads, molecules, biomolecules, microorganisms, cells, for example, bacteria, viruses, DNA fragments, blood cells, constituent of whole blood, etc. Particles may scatter excitation light directly or fluoresce when illuminated by light of an appropriate wavelength. In some cases, the fluorescent emission properties are optimized for specific measurements by attaching probe molecules to the entire particles or to microscopic structures within the particles.

Figure 1:
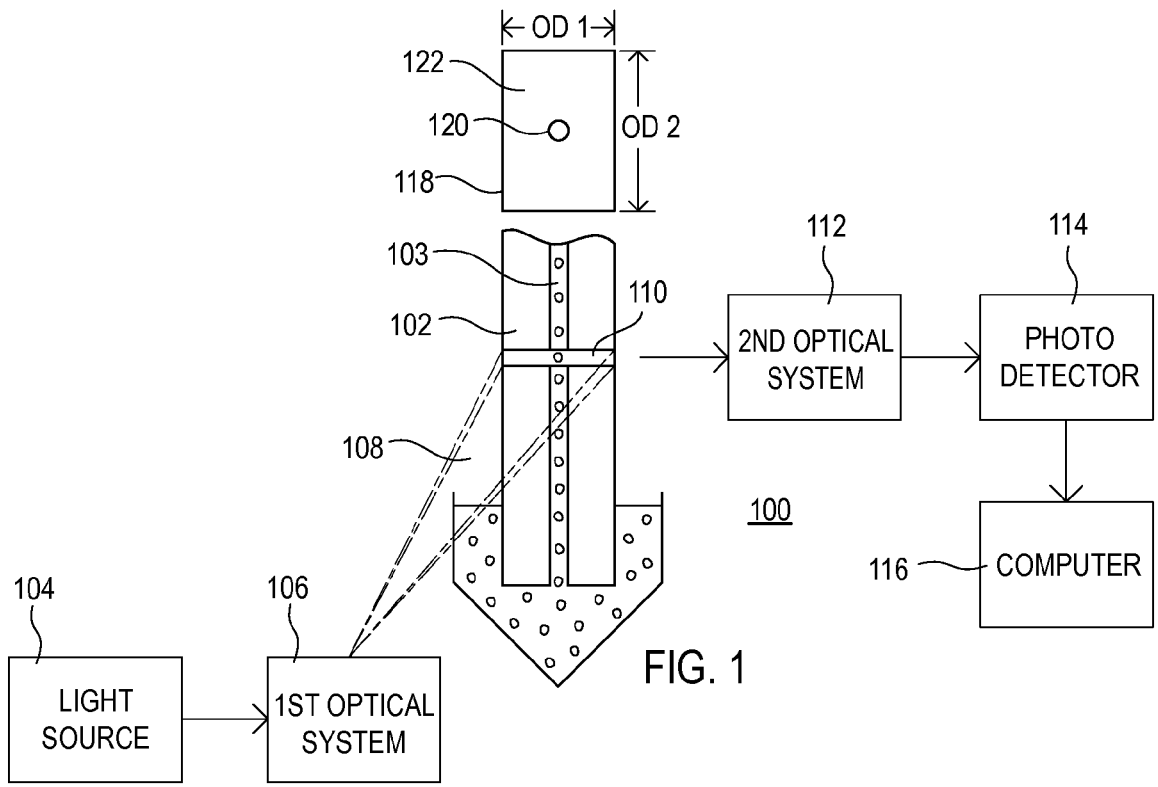
FIG. 1 is a schematic representation of a particle analyzing apparatus in accordance with some embodiments of the invention.

FIG. 1 is a schematic representation of a particle analyzing apparatus 100 in accordance with some embodiments of the invention. In general, the apparatus 100 includes a capillary 102, a light source 104, a first optical system 106 for directing, shaping, and focusing a light beam 108 to the capillary 102 to define an analyzing region 110, a second optical system 112 for collecting, color splitting, and guiding light to photo detectors 114, and an electronic system 116 for processing and analyzing the light signals detected by the photo detectors 114.

The capillary 102 is configured to pass a fluid containing particles to be analyzed. In some embodiments, a fluidics system (not shown) may be coupled to the capillary 102 for transporting a sample fluid through the capillary 102. The fluidics system may include a pump configured to draw the sample fluid from a suspended end of the capillary. Alternatively, a pump may be coupled to an end of the capillary and configured to push the sample fluid through the capillary. By way of example, calibrated pumps such as a syringe pump may be used to draw or push a sample fluid through the capillary at an approximately constant rate.

The capillary 102 can be made from glass, or other materials such as quarts, fused silica, plastics, etc. which provide good optical clarity. The capillary 102 has a wall extending in a longitudinal direction defining a bore 103 for passing particles contained in a fluid. In some embodiments, the size of the capillary bore 103 is selected such that particles in the fluid are singulated as they pass through an analyzing region 110. In some embodiments, the size of the capillary bore 103 is selected such that it is not readily clogged by aggregated particles or particles of various sizes. In general, the size of the capillary bore 103 may range from 50 to 150 micrometers.

The capillary 102 may have an external wall surface 118 and an internal wall surface 120 of suitable configurations defining a cross-section 122 transverse to the longitudinal direction of the capillary. By way of example, the cross-section 122 of the capillary 102 may have a rectangular or square outer shape and a rectangular, square, or circular inner shape. Alternatively, the cross-section 122 of the capillary 102 may have a circular external shape and a rectangular, square, or circular internal shape. Various other combinations of regular or irregular outer and inner shapes of the capillary cross-section 122 are possible, including triangular, trapezoidal, hemispherical, and rhomboid outer or inner shapes. In some preferred embodiments, the cross-section 122 of the capillary 102 may have a rectangular outer shape providing substantially flat surfaces for attaching optical elements to the capillary as described in greater detail below. In some embodiments, the external wall surface 118 of the capillary 102 may include an opaque coating. An area of the opaque coating may be removed to allow a beam of light to project through defining an analyzing region in the capillary.

The light source 104 can be any suitable sources that can provide a beam of light of a selected wavelength suitable to excite the particles or substances labeled to the particles to fluoresce. Suitable light sources include lasers, arc lamps, light-emitting diodes, etc. Lasers can produce coherent light of a single wavelength. Arc lamps are less expensive and can be used in conjunction with optical filters to produce light of a narrow wavelengths band. Incident light wavelengths useful for excitation can range from 300 nm to 1000 nm. Exemplary useful incident light wavelengths include, but are not limited to, wavelengths of at about 300, 350, 400, 450, 500, 550, 600, 700, 800 or 900 nm. Exemplary useful incident light region include, but are not limited to, 350 nm to 450 nm, 450 nm to 500 nm, 500 nm to 550 nm, 550 nm to 600 nm, 600 nm to 700 nm, and 700 nm to 1000 nm. By way of example, specific incident light wavelengths can be 375 nm, 405 nm, 488 nm, 532 nm, 640 nm. One or more light sources with suitable combination of output wavelength and brightness may be included in a single particle analyzing apparatus.

In some embodiments, a first optical system 106 may be used to provide and direct a focused excitation beam 108 onto the capillary 102 to define an analyzing region 110. The first optical system 106 may include one or more optical components such as diffractive, reflective, and refractive optics (not shown). An optional bandpass filter (not shown) with high transmission at the excitation wavelength may be placed between the light source 106 and the analyzing region 110 to block light emitted by the source at wavelengths different from the excitation wavelength. In some embodiments, the first optical system 106 may be configured to project a sheet like beam onto the capillary 102. In some embodiments, the beam 108 incident on the capillary 102 can be shaped and/or sized to have a generally rectangular or elliptical cross section in the longitudinal direction of the capillary. In some embodiments, a generally rectangular or elliptical cross section of the beam incident on the capillary may have a greater dimension that is equal to or greater than the bore size of the capillary. In some embodiments, a generally rectangular or elliptical cross section of the incident beam may have a smaller dimension that is equal to or smaller than the bore size of the capillary. In some embodiments, a generally rectangular or elliptical cross section of the beam incident on the capillary may have a greater dimension that is equal to or greater than the bore size of the capillary, and a smaller dimension that is equal to or smaller than the bore size of the capillary. By way of example, the beam 108 projected onto the capillary 102 may have a generally rectangular or elliptical cross section with a greater dimension from 100 to 1000 micrometers, and a smaller dimension from 5 to 50 micrometers.

The analyzing region 110 may be defined by the internal wall surface 120 of the capillary 102 and the incident beam 108 through the capillary 102. Particles interact with the incident excitation beam 108 within the analyzing region 110 where processes such as fluorescence excitation, small-angle scattering, and large-angle scattering etc. occur. Scatter light and/or fluorescence emitted by the particles or substances labeled to the particles are collected and guided by the second optical system 112, and detected by one or more photo detectors 114 respectively.

The second optical system 112 may include optics arranged at a large angle with respect to the propagation axis of the incident light beam 108 to collect scatter light and fluorescence. The second optical system 112 may include one or more beamsplitters that pass scatter light towards a scatter detector and reflect fluorescent light, or to reflect scatter light and pass fluorescent light. For example, fluorescent light of a first wavelength may pass the first dichroic beamsplitter that reflect the scatter light and be reflected by a second dichroic beamsplitter towards a first fluorescence detector; fluorescent light of a second, different, wavelength may be reflected by a third dichroic beamsplitter towards a second fluorescence detector, and so on. One or more optical bandpass filters (not shown) may be placed between the analyzing region 110 and the detectors 114 to restrict the wavelengths bands reaching each detector.

The second optical system 112 may also include optics to collect forward-scatter light at a small angle with respect to the propagation axis of the incident excitation beam. A beam block may be typically used to prevent the unscattered excitation beam from reaching a forward-scatter light detector. A bandpass filter may be placed between the analyzing region and the forward-scatter light detector to transmit light at the excitation wavelength and to block light at other wavelengths.

The light detectors 114 can be any suitable photon detecting devices such as photomultiplier tubes (PMT), photodiodes, and alternative solid state detectors. In general, photomultiplier tubes are more sensitive for detection of scatter light and fluorescence. Photodiodes are much less expensive and can be used in the construction of the instrument to reduce costs. The light detectors 114 produce pulse signals with amplitudes and temporal profiles that are characteristic of the particles' size, shape, and/or structure etc. A computer or data acquisition and analyzing system 116 typically contains analog to digital convertors (ADCs) to convert the analog light signals into electrical signals for further processing and analysis.

Figure 2:
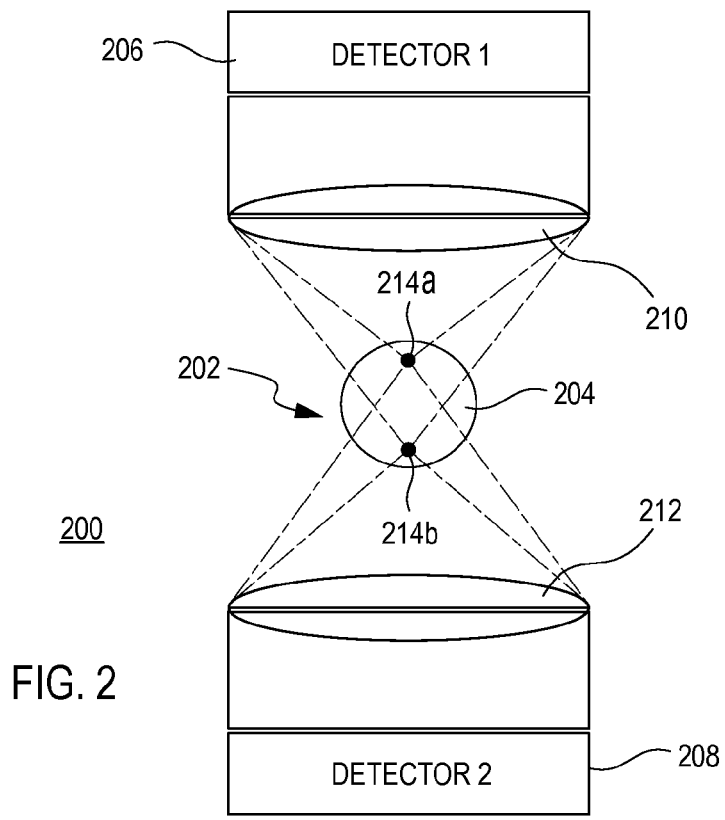
FIG. 2 is a schematic representation of a light collection and detection configuration in a particle analyzing apparatus in accordance with some embodiments showing that light is collected from and detected on both and opposite sides of the capillary.

FIG. 2 is a schematic representation of a light collection and detection configuration in a particle analyzing apparatus 200 in accordance with some embodiments. In addition to a light source and a first optical system for focusing and directing an excitation beam, which are not shown in FIG. 2 for clarity in the illustration and description of the embodiment, the particle analyzing apparatus 200 may include a capillary 202 having an internal wall surface defining an analyzing region 204, a first detector 206 and a second detector 208 arranged opposite to each other. Collecting optics 210, 212 with color selecting filters may be disposed between the analyzing region 204 and the first and second detectors 206, 208. An electronic system (not shown in FIG. 2) may be coupled to the first and second detectors 206, 208 for processing and analyzing light signals detected by the first and second detectors 206, 208. As shown, a particle 214 at the analyzing region 204 may be located at any position relative to a longitudinal axis of the capillary (perpendicular to the plane of the paper). Reference numbers 214a and 214b represent two exemplary positions of the particle 214 within the analyzing region 204. Fluorescence and/or scatter light from the illuminated particle 214 are collected from both opposite sides of the analyzing region 204, and detected by the first and second detectors 206, 208 simultaneously. The light signals detected by the first and second detectors 206, 208 can be summed and further processed and analyzed by an electronic system.

Figure 4:
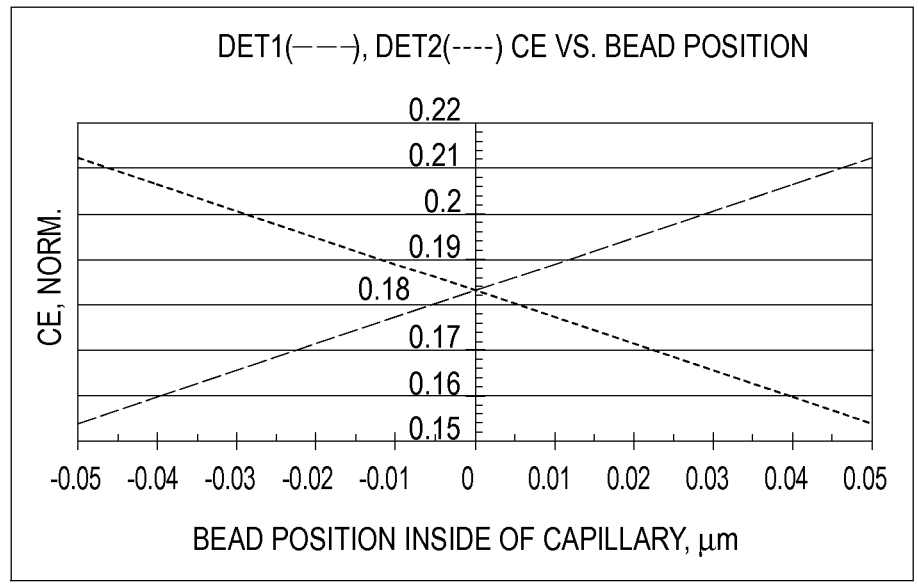
FIG. 4 shows the dependency of light collection efficiency on the particle position within an analyzing region inside a capillary for the configuration shown in FIG. 2.
Figure 5:
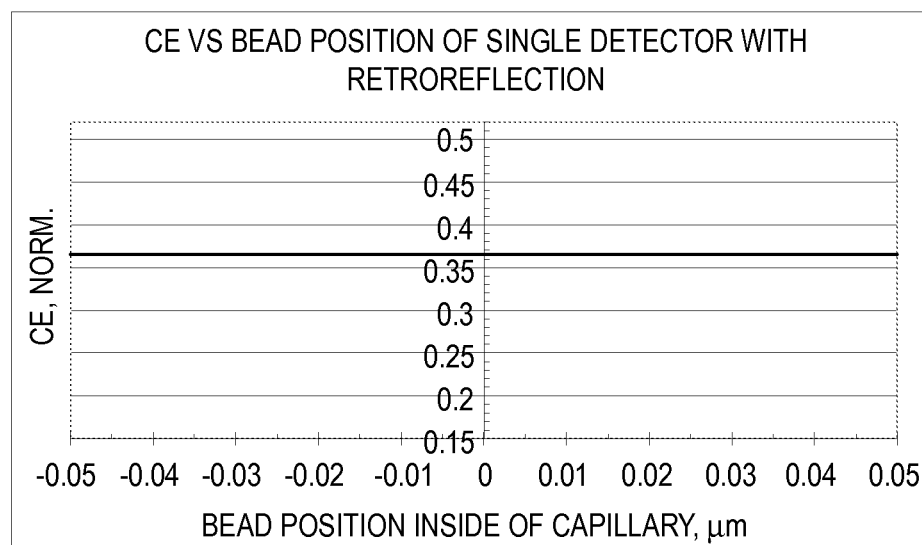
FIG. 5 shows the non-dependency of light collection efficiency on the particle position within an analyzing region inside a capillary for the configuration shown in FIG. 3.

The light collection and detection arrangement shown in FIG. 2 can advantageously increase both the collection efficiency and detection resolution of the particle analyzing apparatus 200. As stated above, light collection in conventional capillary based flow cytometry is sensitive to the position of the particle within the analyzing region inside the capillary. The charts in FIG. 4 demonstrate that the collection efficiency (vertical axis) of individual light detectors 206, 208 changes as a function of the position of the particle 214 within the analyzing region 204 inside the capillary 202 (horizontal axis). However, if the fluorescence and/or the scatter light are collected from both opposite sides of the analyzing region as shown, and summed, then the collection efficiency does not depend on the particle position within the analyzing region inside the capillary as demonstrated by the chart in FIG. 5 which shows that the collection efficiency (vertical axis) of the sum signals form light detectors 206 and 208 does not depend on the position of the particle 214 within the analyzing region 204 inside the capillary 202 (horizontal axis).

Figure 3:
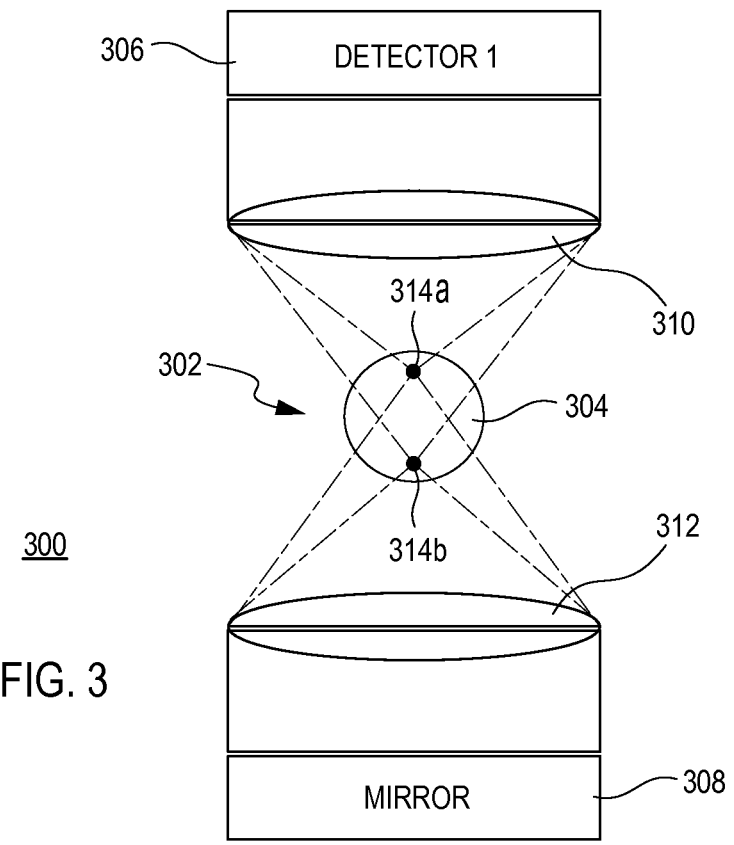
FIG. 3 is a schematic representation of a light collection and detection configuration in a particle analyzing apparatus in accordance with some other embodiments showing that light is collected from both and opposite sides of the capillary but detected on one side using a mirror in retro-reflecting configuration.

FIG. 3 is a schematic representation of another light collection and detection configuration in a particle analyzing apparatus 300 in accordance with some other embodiments. In addition to a light source and a first optical system for focusing and directing an excitation beam, which are not shown in FIG. 3 for clarity in illustration and description of the embodiment, the particle analyzing apparatus 300 may include a capillary 302 having an internal wall surface defining an analyzing region 304, a first light detector 306 configured to detect fluorescence of a wavelength, and a reflection element 308 arranged opposite to first light detector 306 configured to reflect fluorescence of at least the wavelength that is same as that detected by the first light detector 306. Collecting optics 310, 312 may be disposed between the analyzing region 304 and the first light detector 306, and between the analyzing region 304 and the reflection element 308. An electronic system (not shown in FIG. 3) may be coupled to the first light detector 306 for processing and analyzing light signals detected by the first detector. Reference numbers 314a and 314b represent two exemplary positions of the particle 314 within the analyzing region 304. As shown, the first light detector 306 detects fluorescent light collected by both the first collecting lens 310 and the second collecting lens 312 via the reflection element 308. Similar to the embodiment shown in FIG. 2, the collection and detection arrangement shown in FIG. 3 can advantageously increase both the collection efficiency and detection resolution of the particle analyzing apparatus 300. This is demonstrated by the chart in FIG. 5 which shows that the collection efficiency (vertical axis) of the first light detector 306 does not depend on the position of the particle 314 within the analyzing region 304 inside the capillary 302 (horizontal axis).

Figure 6:
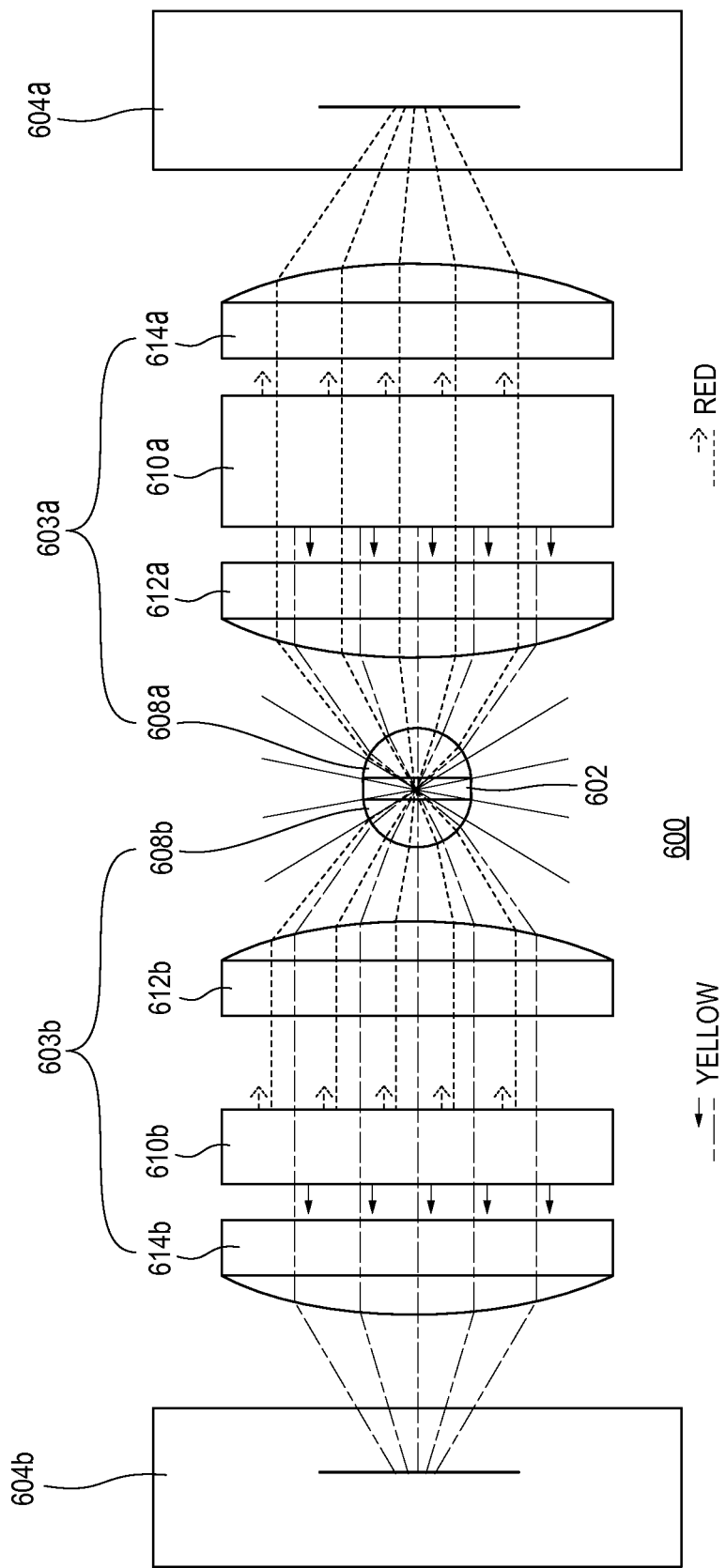
FIG. 6 is a schematic representation of a light collection and detection configuration in a particle analyzing apparatus in accordance with some embodiments.

FIG. 6 is a schematic representation of a light collection and detection configuration in a particle analyzing apparatus 600 in accordance with some other embodiments. The particle analyzing apparatus 600 comprises a light source and a first optical system for focusing and directing an excitation beam (not shown in FIG. 6), and a capillary 602 configured to pass a fluid containing particles to be analyzed. The particle analyzing apparatus 600 further comprises a second optical system 603 configured to collect fluorescent light emitted by a particle or substance labeled to the particle, a first detector 604a, and a second detector 604b.

In some embodiments, the second optical system 603 may include a first collection arm 603a comprising a first collection lens 608a at a first side of the capillary 602, a first collimating lens 612a, and a first reflection element 610a at the same side as the first collection lens 608a. The first collection lens 608a and the first collimating lens 612a are configured to collect light emitted by particles from the first side. The first reflection element 610a is configured to reflect fluorescent light of one or more wavelengths collected and transmit the non-reflected portion of fluorescent light. The first detector 604a is configured to detect fluorescent light of a wavelength collected by the first collection lens 608a and first collimating lens 612a and transmitted through the first reflection element 610a.

In some embodiments, the second optical system 603 may further include a second collection arm 603b comprising a second collection lens 608b at a second side of the capillary 602 opposite to the first side, a second collimating lens 612b, and a second reflection element 610b at the same side as the second collection lens 608b. The second collection lens 608b and the second collimating lens 612b are configured to collect light emitted by particles from the second side. The second reflection element 610b is configured to reflect fluorescent light of one or more wavelengths collected and transmit the non-reflected portion of fluorescent light. The second detector 604b is configured to detect fluorescent light of a wavelength collected by the second collection lens 608b and second collimating lens 612b and transmitted through the second reflection element 610b.

The fluorescent light reflected back by the first reflection element 610a may travel through the first collimating lens 612a, first collecting lens 608a, capillary 602, second collecting lens 608b, second collimating lens 612b, and second reflection element 610b, and may be detected by the second detector 604b. Similarly, the fluorescent light reflected back by the second reflection element 610b may travel through the second collimating lens 612b, second collecting lens 608b, capillary 602, first collecting lens 608a, first collimating lens 612a, and first reflection element 610a, and may be detected by the first detector 604a. The arrangement shown in FIG. 6 can lead to preserving resolution of the instrument while increasing collection efficiency from emitting particles distributed within the capillary bore.

In some embodiments, at least one of the first and second collection lenses 608a, 608b may be coupled to the capillary 602. The first and/or second collection lenses 608a, 608b may be coupled to the capillary 602 by optical contact or with a substance, e.g., optical adhesives, films, and liquids such as immersive oils, etc. Optical contact may occur when two surfaces of transparent bodies are brought together at a distance of the order of the action range of the molecular forces. Bringing the surfaces together to this distance may be referred to as setting them in optical contact. Clean, well-polished surfaces generally can be brought easily into optical contact for the adhesion to be extremely durable without any glue. The substance that may be used to couple the first and/or second collection lenses 608a, 608b to the capillary 602 preferably has a refractive index that substantially matches with the refractive index of the capillary 602. The capillary 602 may have any suitable configurations. For example, the cross-section of the capillary 602 may have a rectangular, square, circular, elliptical or other regular or irregular outer shape, and a rectangular, square, circular, elliptical or other regular or irregular inner shape.

In some embodiments, at least one of the first and second collection lenses 608a, 608b may be integrated with the capillary 602. For example, one or both of the collection lenses 608a, 608b may be adhered to the capillary 602 by optical adhesives. In some embodiments, the capillary 602 may have a rectangular configuration providing substantially flat external wall surfaces, and the first and/or second collection lenses 608a, 608b may also have a planar surface respectively. As such, the first and/or second collection lenses 608a, 608b may be integrated with the capillary through their planar surfaces using e.g. optical adhesives.

In some embodiments, the first reflection element 610a may be a bandpass filter or a dichroic mirror or the like configured to reflect fluorescent light of one or more wavelengths and transmit fluorescent light of wavelength(s) that is (are) different from the one or more wavelengths reflected by the first bandpass filter or dichroic mirror. In some embodiments, the second reflection element 610b may be also a bandpass filter or a dichroic mirror or the like configured to reflect fluorescent light of one or more wavelengths that are same as those transmitted by the first bandpass filter or dichroic mirror 610a and transmit fluorescent light of wavelength(s) that is (are) same as those reflected by the first bandpass filter or dichroic mirror 610a.

In some embodiments, collimating lens 612a and field lens 614a may be placed between the first collection lens 608a and the first detector 604a for collimating and focusing the collected light to the first detector 604a. Collimating lens 612b and field lens 614b may also be placed between the second collection lens 608b and the second detector 604b for collimating and focusing the collected light to the detector 604b.

In operation, an excitation beam from a light source is focused and directed to the capillary 602 to define an analyzing region in the capillary. For example, the excitation beam projected through the capillary 602 may have a generally rectangular cross-section in the longitudinal direction of the capillary, with a greater dimension equal to or greater than the bore size of the capillary and a smaller dimension equal to or smaller than the bore size of the capillary. A sample fluid containing particles to be analyzed is transported through the analyzing region where fluorescence excitation, absorption, small-angle scattering, and large-angle scattering etc. occur as the particles interact with the incident excitation beam. Fluorescence emitted by the particles or substances labeled to the particles emit in all directions as shown. The first collection lens 608a collects fluorescent light at the first side of the capillary 602 and the second collection lens 608b collects fluorescent light at the second side of the capillary 602. The fluorescent light collected by the first collection lens 608a is collimated and directed to the first detector 604a configured to detect fluorescence of a first wavelength e.g. red. The fluorescent light collected by the second collection lens 608b is collimated and directed to the second detector 604b configured to detect fluorescence of a second wavelength e.g. yellow. The first reflection element 610a disposed at the same side as the first collection lens 608a may be configured to transmit fluorescence of the first wavelength e.g. red, and reflect fluorescence of the second wavelength e.g. yellow which is further directed to the second detector 604b. The second reflection element 610b at the side of the second collection lens 608b may be configured to transmit fluorescence of the second wavelength e.g. yellow, and reflect fluorescence of the first wavelength e.g. red which is further directed to the first detector 604a. With the configuration shown in FIG. 6, the first detector 604a may detect fluorescent light of a first wavelength e.g. red that is collected by both the first collection lens 608a and the second collection lens 608b. The second detector 604b may detect fluorescent light of a second wavelength e.g. yellow that is collected by both the second collection lens 608b and the first collection lens 608a.

Advantageously, the particle analyzing apparatus in accordance with the above embodiments can increase the collection efficiency of the instrument to at least 30%, which is at least 10 times of that of a conventional capillary based flow cytometry. The increased collection efficiency is achieved without sacrificing the resolution of the instrument. The increased collection efficiency significantly improves the sensitivity and enhances the dynamic range and throughput of the instrument. As a result of the improved collection efficiency, light detectors that are less expensive and have relatively low sensitivity may be used in a particle analyzing apparatus to reduce the construction cost of the instrument and to obtain instrument performance comparable to that of the prior art.

Figure 7:
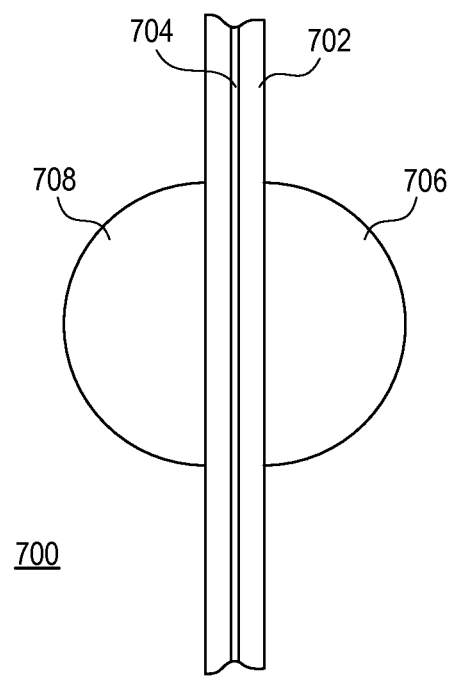
FIG. 7 is a schematic representation of a flow cell including a capillary integrated with two micro lenses in accordance with some embodiments.

FIG. 7 is a schematic representation of a flow cell 700 in accordance with some embodiments. The flow cell 700 includes a capillary 702 having a wall extending in a longitudinal direction defining a bore 704, and a first collection lens 706 attached to the wall of the capillary 702. The first collection lens 706 may be configured to collect fluorescent and/or scatter light from a particle or substance labeled to the particle. In some embodiments, the flow cell 700 may further include a second collection lens 708 attached to the wall of the capillary 702. The first and second collection lenses 706, 708 may be disposed opposite to each other. In some embodiments, the first and second collection lenses 706, 708 may be micro lenses integrated with the capillary 702. The integration of the micro lenses with the capillary can be achieved using any suitable means. By way of example, micro lenses can be adhered to the capillary using adhesives, films, liquids etc. Optical adhesives such as commercially available UV-light curable optical adhesives can be used. Preferably, the optical adhesives are selected to provide high-strength bonds between the lenses and capillary and to provide good light transmission properties. Preferably the refractive index of the adhesives selected matches the refractive index of the material making the capillary and has low auto-fluorescence. Alternative means may be used to integrate micro lenses 706, 708 with the capillary 702.

In some embodiments, the capillary 702 may have a rectangular or square configuration providing planar external wall surfaces for ease of integration with the first and/or second collection lenses 706, 708. As such, the first and/or second collection lenses 706, 708 may also have a planar surface to be attached to the planar external wall surface(s) of the capillary 702. The cross-section of the capillary 702 transverse to the longitudinal direction may have a rectangular or square outer shape and a rectangular, square, or circular inner shape. For example, in some preferred embodiments, the capillary 702 may have a cross-section with a rectangular outer shape and a circular or square inner shape. The cross section of the capillary may also have triangular, trapezoidal, hemispherical, and rhomboid outer or inner shapes. Various alternative configurations of the capillary 702 and the first and/or second collection lenses 706, 708 are possible and contemplated by the invention. By way of example, the capillary 702 may have a cross-section having a rectangular outer shape with a dimension of 0.8 mm×1.5 mm, and a circular inner shape with a diameter of about 100 micrometers.

Figure 8:
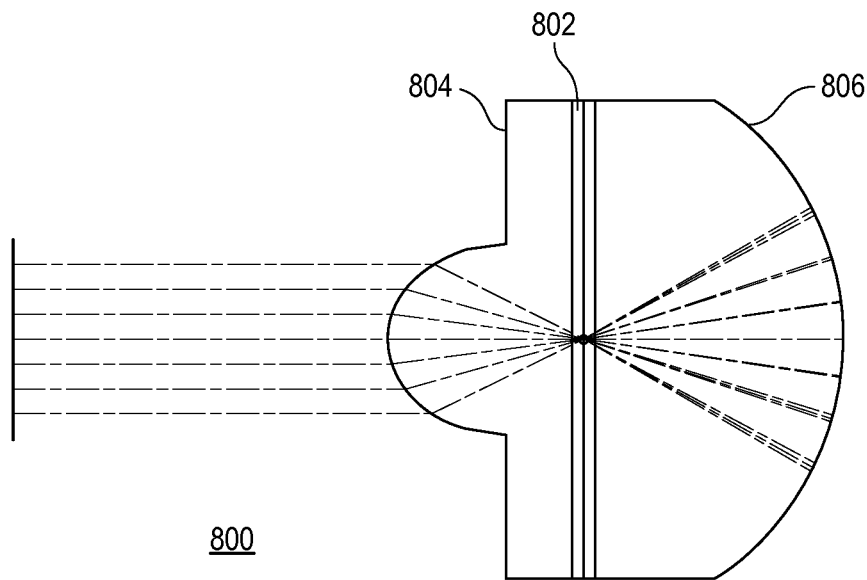
FIG. 8 is a schematic representation of a flow cell including a capillary integrated with a collection lens and a reflection mirror in accordance with some embodiments.

FIG. 8 illustrates an alternative embodiment of a flow cell 800. The flow cell 800 includes a capillary 802 having a wall extending in a longitudinal direction defining a bore, a first collection lens 804 attached to the wall of the capillary 802 configured to collect fluorescent light and/or scatter light, and a reflection element 806 attached to the capillary 802 opposite to the first collection lens 804. The reflection element 806 may include a coating on the curved surface configured to reflect fluorescent light of one or more wavelengths. The first collection lens 804 and reflection element 806 may be integrated with the capillary 802 using optical adhesives as described above, or using any other alternative means known in the art. By way of example, capillary-lens integration embodying the features of some embodiments may be mass-produced using wafer-scale techniques of Monolithic Lens Molding. Such techniques are, for example, practiced commercially by Anteryon BV, P.O. Box 33, 5600 AA Eindhoven, The Netherlands.

The flow cell described and shown in FIG. 7 or FIG. 8 can be supported by a support assembly which can be replaceably mounted in a particle analyzing apparatus. A flow cell assembly including the flow cell shown in FIG. 7 or FIG. 8 may facilitate the replacement of a flow cell with damaged or otherwise broken capillary with an undamaged capillary, or with a flow cell having a capillary of different size or shape.

Figure 9:
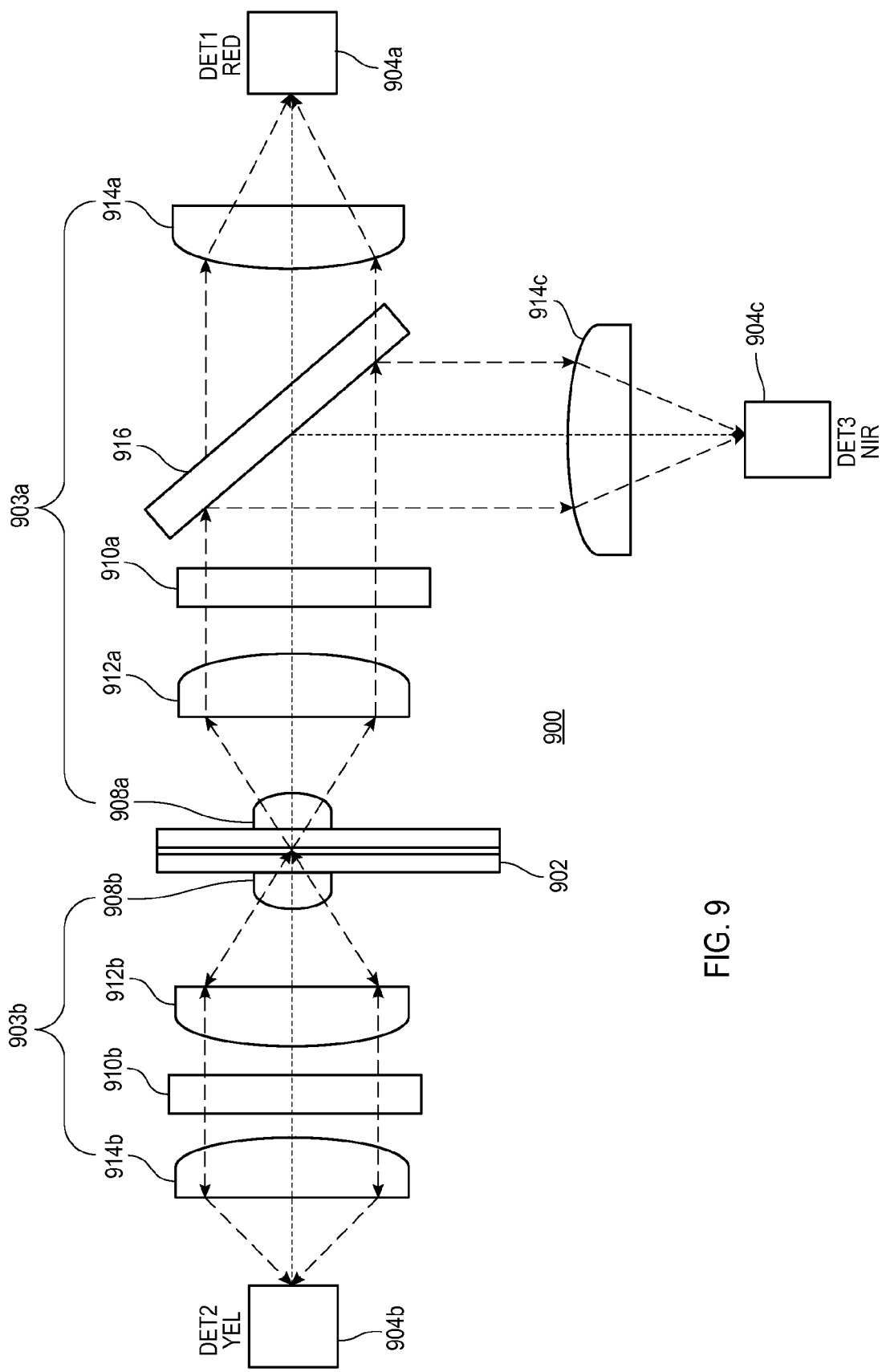
FIG. 9 is a schematic representation of a light collection and detection configuration in a particle analyzing apparatus in accordance with some embodiments.

FIG. 9 is a schematic representation of a light collection and detection configuration in a particle analyzing apparatus 900 in accordance with some other embodiments. In comparison, the light collection and detection configuration of the particle analyzing apparatus 900 is similar to the light collection and detection configuration of the particle analyzing apparatus 600 illustrated in FIG. 6 in many aspects. For example, the light collection system 903 may include a first collection arm 903a at a first side of the capillary 902 and a second collection arm 903b at a second side of the capillary 902, which may be at the opposite side of the first collection arm 903a.

The first collection arm 903a may include a first collection lens 908a, a first collimating lens 912a, a first reflection element 910a, and a first field lens 914a. The first collection lens 908a may be configured to collect light emitted by particles from the first side of the capillary 902. The first reflection element 910a may be configured to reflect fluorescent light of one or more wavelengths collected and transmit the non-reflected portion of fluorescent light e.g. red and/or near infrared (NIR) light. The first detector 904a may be configured to detect fluorescent light of a wavelength e.g. red light transmitted through the first reflection element 910a.

The second collection arm 903b may include a second collection lens 908b, a second collimating lens 912b, a second reflection element 910b, and a second field lens 914b. The second collection lens 908b may be configured to collect light emitted by particles from the second side of the capillary 902. The second reflection element 910b may be configured to reflect fluorescent light of one or more wavelengths collected and transmit the non-reflected portion of fluorescent light e.g. yellow light. The second detector 904b may be configured to detect fluorescent light of a wavelength e.g. yellow light transmitted through the second reflection element 910b.

The fluorescent light back-reflected by the first reflection element 910a may travel through the first collimating lens 912a, first collecting lens 908a, capillary 902, second collecting lens 908b, second collimating lens 912b, and second reflection element 910b, and may be detected by the second detector 904b. Likewise, the fluorescent light back-reflected by the second reflection element 910b may travel through the second collimating lens 912b, second collecting lens 908b, capillary 902, first collecting lens 908a, first collimating lens 912a, and first reflection element 910a.

In comparison with the embodiment illustrated in FIG. 6, the light collection and detection configuration illustrated in FIG. 9 may further include one or more additional reflection elements and one or more additional detectors which may be beneficial for a multi-channel instrument to detect increased numbers of fluorescent colors. As shown in FIG. 9, an additional reflection element such as a dichroic mirror 916 may be placed between the first reflection element 910a and the first detector 904a. The dichroic mirror 916 may be positioned at an angle such as e.g. 45 degrees with respect to the collimation direction. The dichroic mirror 916 may be configured to reflect fluorescent light of a wavelength e.g. near infrared and transmit fluorescent light of a wavelength e.g. red. The red light transmitted through the dichroic mirror 916 may be detected by detector 904a. The near infrared light reflected by the dichroic mirror 916 may be detected by the additional detector 904c. A field lens 914c may be placed in front of the detector 904c to focus the light into the detector.

Figure 10:
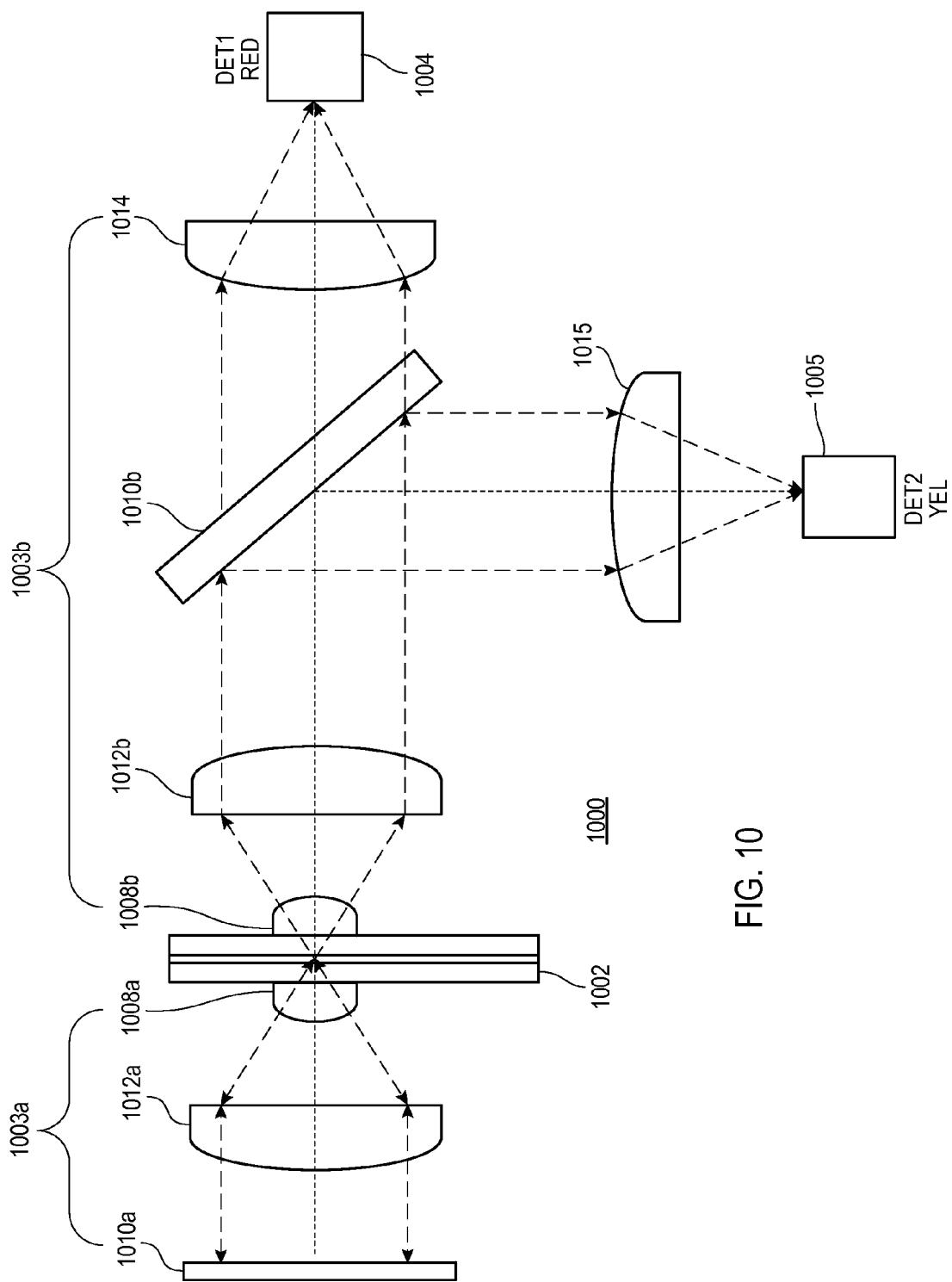
FIG. 10 is a schematic representation of a light collection and detection configuration in a particle analyzing apparatus in accordance with some other embodiments.

FIG. 10 is a schematic representation of a light collection and detection configuration in a particle analyzing apparatus 1000 in accordance with some other embodiments. In comparison with the embodiment illustrated in FIG. 6, a reflection element 1010a may be used to reflect fluorescent light with a wavelength range of interest. Two or more detectors 1004, 1005 may be placed on a same side with respect to the capillary 1002, which may be beneficial e.g. for packaging instrument components.

The particle analyzing apparatus 1000 may include a light source and a first optical system for focusing and directing an excitation beam (not shown in FIG. 10), and a capillary 1002 configured to pass a fluid containing particles to be analyzed. The particle analyzing apparatus 1000 may include a second optical system 1003 configured to collect fluorescent light emitted by particles or substance labeled to the particles, and a first detector 1004 and a second detector 1005 which may be placed on the same side with respect to the capillary 1002. The second optical system 1003 may include a first collection arm 1003a at a first side of the capillary 1002 and a second collection arm 1003b at a second side of the capillary 1002, which may be the opposite side of the first collection arm 1003a.

The first collection arm 1003a may include a first collection lens 1008a, a first collimating lens 1012a, and a first reflection element 1010a. The first collection lens 1008a may be configured to collect light emitted by particles from the first side of the capillary 1002. The first reflection element 1010a may be configured to back-reflect fluorescent light collected. By way of example, the first reflection element 1010a may be a 100% mirror which may be configured to reflect fluorescent light having wavelengths ranging from 300 nm to 1000 nm, or ranging from 350 nm to 950 nm, or ranging from 400 to 900 nm etc, or any range of wavelengths of interest.

The second collection arm 1003b may include a second collection lens 1008b at a second side of the capillary 1002 opposite to the first side, a second collimating lens 1012b, and a second reflection element 1010b. The second collection lens 1008b may be configured to collect light emitted by particles from the second side. The second reflection element 1010b may be a dichroic filter, which may be positioned at an angle such as e.g. 45 degrees with respect to the collimation direction. The dichroic filter 1010b may be configured to reflect fluorescent light of a wavelength e.g. yellow light and transmit fluorescent light of a wavelength e.g. red light. The red light transmitted through the dichroic filter 1010b may be detected by the first detector 1004. The yellow light reflected by the dichroic mirror 1010b may be detected by the second detector 1005. Field lenses 1014, 1015 may be placed in front of the detectors 1004, 1005 to focus the light into the detectors. It will be appreciated by one of ordinary skill in the art that two or more dichroic filters may be added to increase the number of colors that can be detected in a multi-channel instrument.

Those skilled in the art will appreciate that various other modifications may be made within the spirit and scope of the invention. All these or other variations and modifications are contemplated by the inventors and within the scope of the invention.

What is claimed is:

1. A particle analyzing apparatus comprising:
a capillary configured to pass a fluid containing particles to be analyzed, said particles fluoresce or are labeled with substances that fluoresce upon illumination of light;
a source of light;
a first optical system configured to direct a beam of light through the capillary to define an analyzing region in capillary;
a second optical system configured to collect fluorescent light emitted from a particle or substance labeled to the particle in the analyzing region, wherein the second optical system has an optical axis, and comprises a first collection lens attached to a first side of the capillary adjacent to the analyzing region, and a first reflection element arranged adjacent to the first collection lens configured to reflect back fluorescent light of one or more wavelengths in a direction parallel with the optical axis and transmit fluorescent light of wavelength(s) that is (are) different from the one or more wavelengths reflected by the first reflection element; and
a first detector configured to detect fluorescent light transmitted through the first reflection element.

2. The particle analyzing apparatus of claim 1 wherein
the second optical system further comprises a second collection lens attached to a second side of the capillary opposite to the first side, and a second reflection element arranged adjacent to the second collection lens and configured to reflect back fluorescent light of one or more wavelengths in a direction parallel with the optical axis and transmit fluorescent light of wavelength(s) that is (are) different from the one or more wavelengths reflected by the second reflection element; and
the particle analyzing apparatus further comprising a second detector configured to detect fluorescent light transmitted through the second reflection element.

3. The particle analyzing apparatus of claim 2 wherein:
the first reflection element is configured to reflect back fluorescent light of one or more wavelengths that are transmittable by the second reflection element, and transmit fluorescent light of wavelength(s) that are reflectible by the second reflection element; and
the second reflection element is configured to reflect back fluorescent light of one or more wavelengths that are transmittable by the first reflection element, and transmit fluorescent light of wavelength(s) that are reflectible by the first reflection element.

4. A particle analyzing apparatus comprising:
a capillary configured to pass a fluid containing particles to be analyzed, said particles fluoresce or are labeled with substances that fluoresce upon illumination of light;
a source of light;
a first optical system configured to direct a beam of light through the capillary to define an analyzing region in capillary;
a second optical system configured to collect fluorescent light emitted from a particle or substance labeled to the particle in the analyzing region, wherein the second optical system comprises:
a first collection lens at a first side of the capillary adjacent to the analyzing region, and a first reflection element arranged adjacent to the first collection lens configured to reflect fluorescent light of one or more wavelengths and transmit fluorescent light of wavelength(s) that is (are) different from the one or more wavelengths reflected by the first reflection element;

a second collection lens at a second side of the capillary opposite to the first side, and a second reflection element arranged adjacent to the second collection lens and configured to reflect fluorescent light of one or more wavelengths and transmit fluorescent light of wavelength(s) that is (are) different from the one or more wavelengths reflected by the second reflection element;

the first reflection element is configured to reflect fluorescent light of one or more wavelengths that are transmittable by the second reflection element, and transmit fluorescent light of wavelength(s) that are reflectible by the second reflection element; and the second reflection element is configured to reflect fluorescent light of one or more wavelengths that are transmittable by the first reflection element, and transmit fluorescent light of wavelength(s) that are reflectible by the first reflection element;

a first detector configured to detect fluorescent light transmitted through the first reflection element;

a second detector configured to detect fluorescent light transmitted through the second reflection element;

wherein the second optical system further comprises a first collimating lens arranged between the first collection lens and the first reflection element, and a second collimating lens arranged between the second collection lens and the second reflection element.

5. The particle analyzing apparatus of claim 3 wherein the second optical system further comprises a third reflection element arranged adjacent to the first reflection element and configured to reflect fluorescent light of a wavelength transmitted from the first reflection element in a direction that is unparallel with the optical axis and transmit fluorescent light of a wavelength transmitted from the first reflection element; and the particle analyzing apparatus further comprises a third detector configured to detect fluorescent light reflected by the third reflection element.

6. The particle analyzing apparatus of claim 5 wherein the third reflection element is a dichroic filter and placed at an oblique angle with respect to an optical axis.

7. A particle analyzing apparatus of claim 1 comprising:
a capillary configured to pass a fluid containing particles to be analyzed, said particles fluoresce or are labeled with substances that fluoresce upon illumination of light;
a source of light;
a first optical system configured to direct a beam of light through the capillary to define an analyzing region in capillary;
a second optical system configured to collect fluorescent light emitted from a particle or substance labeled to the particle in the analyzing region, wherein the second optical system has an optical axis, and comprises a first collection lens attached to a first side of the capillary adjacent to the analyzing region, and a first reflection element arranged adjacent to the first collection lens configured to reflect fluorescent light of one or more wavelengths and transmit fluorescent light of wavelength(s) that is (are) different from the one or more wavelengths reflected by the first reflection element; and
a first detector configured to detect fluorescent light transmitted through the first reflection element; wherein
the second optical system further comprises a second collection lens attached to a second side of the capillary opposite to the first side, and a second reflection element arranged adjacent to the second collection lens, the second reflection element being a mirror configured to back-reflect fluorescent light of wavelengths of a range collected by the second collection lens in a direction parallel with the optical axis; and
the first reflection element is configured to reflect fluorescent light in a direction unparallel with the optical axis; and
the particle analyzing apparatus further comprises a second detector configured to detect the fluorescent light reflected by the first reflection element.

8. The particle analyzing apparatus of claim 7 wherein the first reflection element is a dichroic filter.

9. The particle analyzing apparatus of claim 1 further comprising a fluidic system configured to transport the fluid containing particles to be analyzed through the analyzing region in the capillary.

10. The particle analyzing apparatus of claim 1 further comprising a data acquisition and analyzing system configured to analyze signals of light detected by the first detector.

* * * * *

UNITED STATES PATENT AND TRADEMARK OFFICE
CERTIFICATE OF CORRECTION

PATENT NO. : 8,605,283 B2
APPLICATION NO. : 13/457356
DATED : December 10, 2013
INVENTOR(S) : Fedor Ilkov It is certified that error appears in the above-identified patent and that said Letters Patent is hereby corrected as shown below:

IN THE CLAIMS:

Column 14, line 1, delete "of claim 1"

Signed and Sealed this
First Day of April, 2014

Michelle K. Lee
*Deputy Director of the United States Patent and Trademark Office*